US00PP20105P3

(12) United States Plant Patent
Khanizadeh

(10) Patent No.: US PP20,105 P3
(45) Date of Patent: Jun. 16, 2009

(54) RASPBERRY PLANT NAMED 'JEANNE D'ORLEANS'

(50) Latin Name: *Rubus ideaus L.*
Varietal Denomination: Jeanne d'Orléans

(75) Inventor: Shahrokh Khanizadeh, Quebec (CA)

(73) Assignee: Her Majestry The Queen In Right of Canada, as represented by the Minister of Agriculture and Agri-Food, Lacombe, Alberta (CA)

( * ) Notice: Subject to any disclaimer, the term of this patent is extended or adjusted under 35 U.S.C. 154(b) by 0 days.

(21) Appl. No.: 11/787,954

(22) Filed: Apr. 17, 2007

(65) Prior Publication Data

US 2008/0263733 P1 Oct. 23, 2008

(51) Int. Cl.
*A01H 5/00* (2006.01)

(52) U.S. Cl. ..... Plt./204
(58) Field of Classification Search ..... Plt./204
See application file for complete search history.

(56) References Cited

PUBLICATIONS

Raintree Nursery print out, dated Oct. 22, 2007—"Chill Hours Chart".*

* cited by examiner

*Primary Examiner*—Annette H Para
*Assistant Examiner*—Georgia Helmer
(74) *Attorney, Agent, or Firm*—Klarquist Sparkman, LLP

(57) ABSTRACT

A new and distinct variety of *Rubus idaeus* L. plant, distinguished by greater fruit size, longer shelf life and fruit quality. The candidate variety also has high Soluble Solids (SS) content and high total of Hydrophobic and Crude antioxidant activities.

5 Drawing Sheets

Latin name of the genus and species of the plant claimed: *Rubus idaeus* L.
Variety denomination: 'Jeanne d'Orléans'.

BACKGROUND OF THE INVENTION

The present invention relates to a new and distinct variety of raspberry named 'Jeanne d'Orléans'. The parents of the new and distinct cultivar of the present invention are 'Chilliwack' (unpatented) and 'Meeker' (unpatented).

The instant plant, 'Jeanne d'Orléans', originated from a cross between 'Chilliwack' and 'Meeker', made in 1994 at the Agriculture and Agri-Food Canada, St-Jean-sur-Richelieu, research centre in Quebec. The new cultivar has been found to undergo asexual propagation at L'Acadie, Quebec, Canada by in vitro tissue culture.

Asexual reproduction of this new variety shows that the foregoing and other characteristics come true to form, are firmly fixed, and are established and transmitted through succeeding asexual propagations.

SUMMARY OF THE INVENTION

The 'Jeanne d'Orléans' variety may be distinguished from other raspberry varieties due to the following combination of characteristics: greater fruit size, longer shelf life and fruit quality. The candidate variety also has high Soluble Solids (SS) content and high total of Hydrophobic and Crude antioxidant activities.

The cross was made in 1994 at Agriculture and Agri-Food Canada, St-Jean-sur-Richelieu, research centre in Quebec. Several characteristics including winter hardiness, yield, fruit size and shelf life have been closely monitored since 1995.

BRIEF DESCRIPTION OF THE DRAWINGS

The 'Jeanne d'Orléans' raspberry is illustrated by the accompanying color photographs, taken when the plants were three years old, in which.

Figure 1:
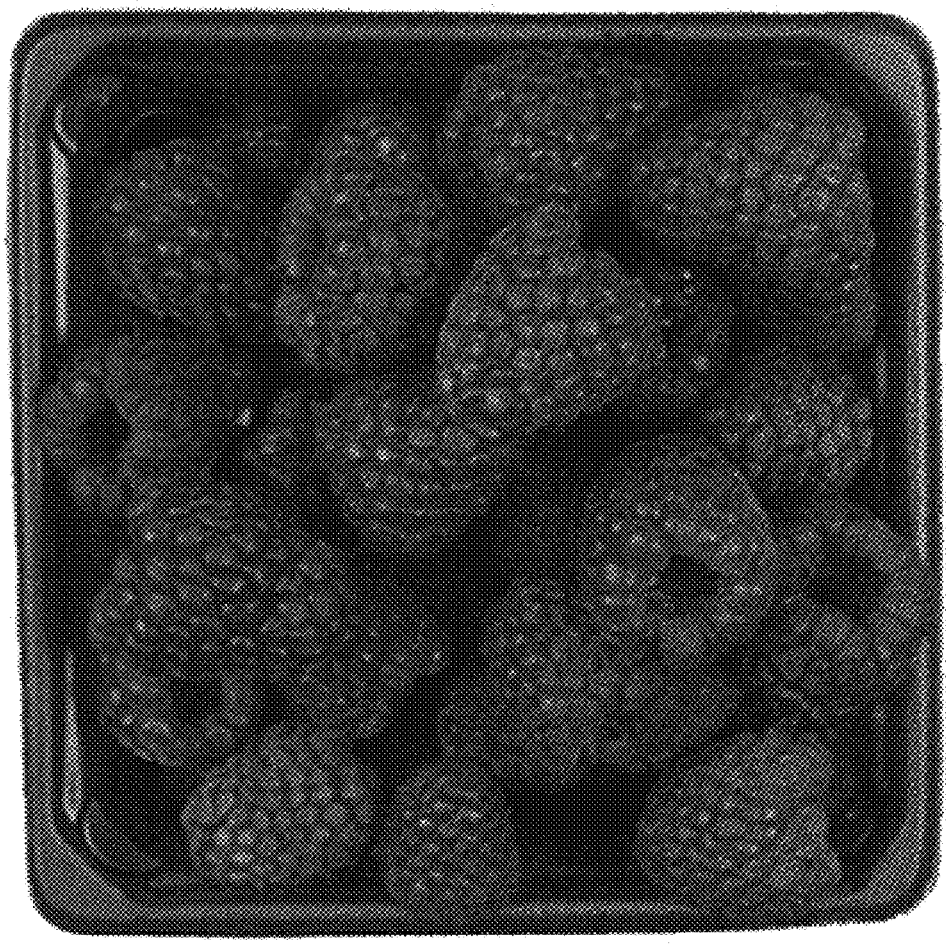
FIG. 1 shows 'Jeanne d'Orléans' fruit.
Figure 2:
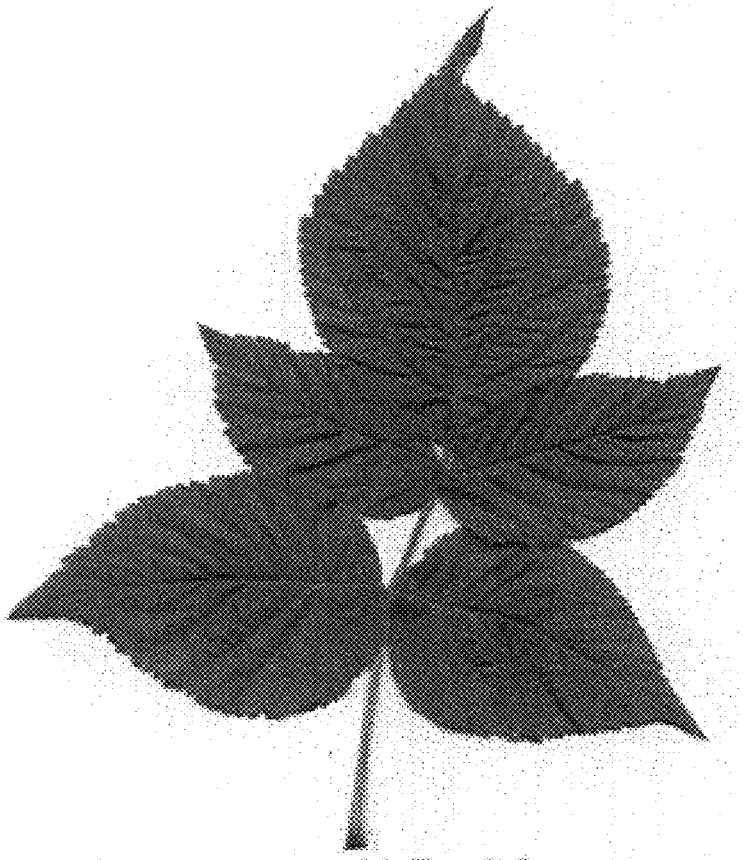
FIG. 2 shows the upper surface of a leaf of 'Jeanne d'Orléans'.
Figure 3:
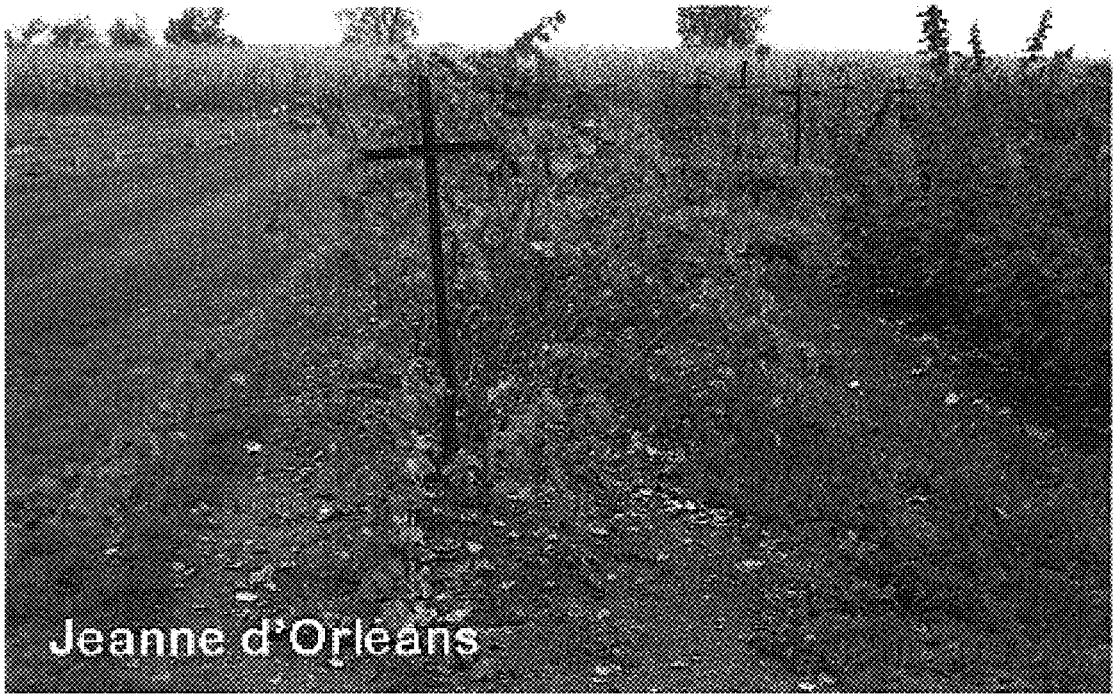
FIG. 3 shows a 'Jeanne d'Orléans' plant.
Figure 4:
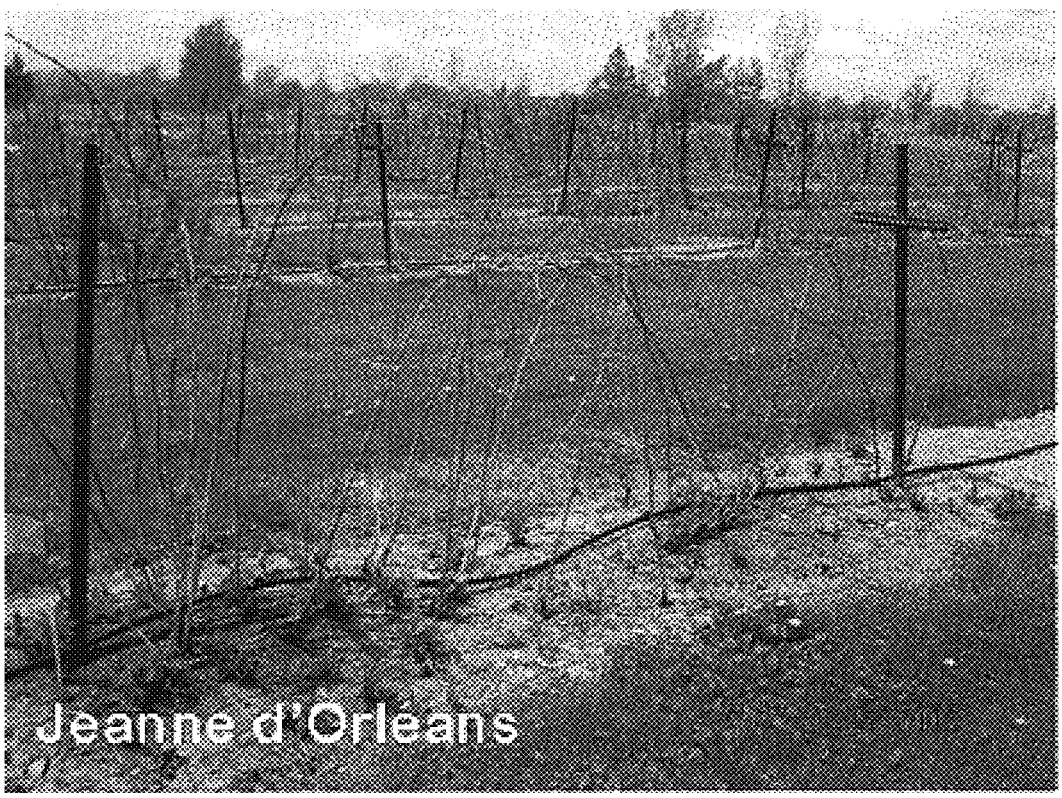
FIG. 4 shows a 'Jeanne d'Orléans' plant in spring.
Figure 5:
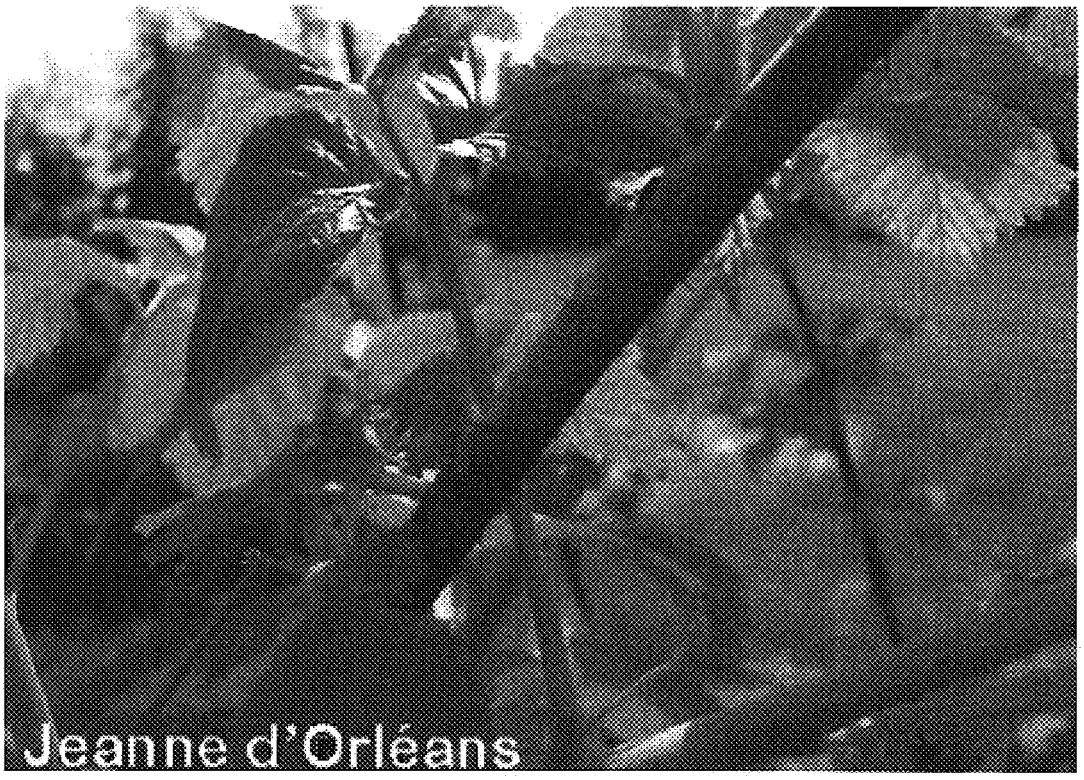
FIG. 5 shows a 'Jeanne d'Orléans' stem with spines.

The colors of an illustration of this type may vary with lighting and other conditions and therefore, color characteristics of this new variety should be determined with reference to the observations described herein, rather than from these illustrations alone.

DETAILED DESCRIPTION

The original variety and progeny have been observed growing in a cultivated area in Québec, Canada. Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart. All color characteristics were determined using the 1986 version of the Royal Horticultural Society (R.H.S.) Colour charts and measured characteristics were based on ten plan measurements. It should be understood that the colors may vary, depending on factors such as growing and lighting conditions.

Scientific Name: *Rubus idaeus* L. 'Jeanne d'Orléans'.

Parentage: 'Meeker' is the seed/female parent. 'Chilliwack' is the pollen/male parent.

Plant characteristics:

*Main fruit bearing type.*—Only on previous year's cane in summer.

*Habit.*—Semi-upright.

*Number of current season's canes observed at the beginning of the second year.*—Few.

Young shoot characteristics: (observed when shoots are 15 cm long).

*Very young shoots.*—Anthocyanin coloration of apex during rapid growth: absent.

Cane characteristics: (observed when the cane is about 1 meter to 1.5 meter long).

*Time of vegetative bud burst.*—Late.

*Current season canes.*—Glaucosity: weak to medium. Anthocyanin coloration: weak. Length of internode: medium. Length of vegetative bud: short.

*Dormant cane length.*—Mean: 113 cm. Range: 64–158 cm. Standard deviation: 34 cm. Number measured: 18.

*Dormant cane color.*—Greyish orange-brown (R.H.S. 199C).

*Spines.*—Density: sparse to medium; spares in central third of 1 year old canes. Size at base: medium. Spine length: medium to long. Spine color: purple (RHS 77A).

Leaf characteristics: (observed filly developed leaves from middle third of the cane).

*Yellow-Green color of upper side.*—RHS 144A.

*Predominant number of leaflets.*—Equally three and five.

*Relief between the veins (rugosity).*—Strong to very strong.

*Relative position of lateral leaflets.*—Slightly overlapping.

*Terminal leaflet length.*—Mean: 20.9 cm. Range: 17.4–23.7 cm. Standard deviation: 1.7 cm. Number measured: 10.

*Terminal leaflet width.*—Mean: 19.3 cm. Range: 17.1–21.0 cm. Standard deviation: 1.3 cm. Number measured: 10.

Flower characteristics:

*Time of beginning of flowering on previous year's cane (10% of flowers have opened).*—Very late.

*Pedicel number of spines.*—Few to medium.

*Peduncle.*—Anthocyanin coloration: present. Intensity of anthocyanin coloration: strong to very strong.

Fruit characteristics: Time of beginning of fruit ripening on previous year's cane — when the fruit is most easily removed from the plug: late

*Fruiting lateral.*—Attitude: erect to semi erect. Length: long.

*Fruit.*—Length: long. Width: broad. Length/width ratio: longer than broad. General shape lateral view: broad conical to conical. Size of single drupe: large. Fruit color: dark red (RHS 53A). Fruit glossiness: weak. Fruit firmness: firm. Adherence to plug: weak to medium.

*Chilling requirement.*—About 900 hours.

Raspberries of 'Jeanne d'Orléans' were compared to 'Boyne' and 'Killarney' raspberry varieties, referred to herein as the "reference varieties." 'Jeanne d'Orléans' can be readily distinguished from 'Boyne' and 'Killarney' by the characteristics listed in Table 1. 'Jeanne d'Orléans' shape is long and conic where as the reference variety's shape is globose. 'Jeane d'Orléans' fruit size is very large compared to 'Boyne' and 'Killarney'. 'Jeanne d'Orléans' glossiness is weak compared to the reference varieties. The shelf life of 'Jeanne d'Orléans' is significant longer compared to 'Boyne' and 'Killarney'. Soluble Solids and Antioxidants are significant higher compared to the reference varieties.

TABLE I : Comparison of Physical Characteristics of 'Jeanne d'Orléans' to Reference Varieties 'Killarney' and 'Boyne'.

| | 'Jeanne d'Orle ans' | 'Killarney' | 'Boyne' |
|---|---|---|---|
| Shape of Fruit | long conic | globose | globose |
| Size of Fruit | very large | small to medium | small |
| Shelf life | significant longer than reference varieties | | |
| Glossiness | weak | Strong | medium |
| Soluble Solids | Significant higher than reference varieties | | |
| Antioxidant | Significant higher than reference Varieties | | |
| Number of current season canes | few | medium-many | many |
| Anthocyanin coloration of apex of very young shoots during rapid growth | absent | Present | present |
| Intensity of Anthocyanin coloration of apex of very young shoots during rapid growth | absent or weak | weak-medium | weak |
| Time of vegetative bud burst | late | Early | early |
| Current season's cane glaucosity | weak-medium | — | medium |
| Current season's cane anthocyanin coloration | weak (when present) | — | medium (when present) |
| Current season's cane length of internode | medium | Short | medium |
| Dormant cane length: | | | |
| Mean: | 113 cm | 110 cm | 106 cm |
| Range: | 64-158 cm | 62-162 cm | 60-158 cm |
| Standard deviation: | 34 cm | 27 cm | 33 cm |
| Dormant cane color: | brown (RHS 199C) | Greyed-orange (RHS 166A) | Greyed-orange (RHS |
| Spine density | sparse-medium | dense | dense |
| Spine length | medium-long | — | medium |
| Spine color | Purple (RHS 77A) | Purple (RHS 77A) | Purple (RHS 77A) |
| Green color of upper side of leaf | Yellow-Green (RHS 144A) | Green (RHS 137A) | Green (RHS 137A) |
| Predominant number of leaflets | equally three and five | usually three | equally three and five |
| Relief between the veins of leaf | strong-very strong | very strong | medium-strong |
| Relative position of lateral leaflets | overlaps with terminal leaflet | overlaps with terminal leaflet | overlaps with terminal leaflet |
| Terminal leaflet length: | | | |
| Mean: | 20.9 cm | 20.6 cm | 21.5 |
| Range | 17.4-23.7 cm | 17.4-23.7 cm | 19.1-25.3 cm |

-continued

| | 'Jeanne d'Orle ans' | 'Killarney' | 'Boyne' |
|---|---|---|---|
| Standard deviation | 1.7 cm | 2 cm | 1.8 cm |
| Terminal leaflet width: | | | |
| Mean: | 19.3 cm | 18.82 cm | 19.8 cm |
| Range: | 17.1-21.0 cm | 17.3-21.2 cm | 17.7-24.8 cm |
| Standard deviation: | 1.3 cm | 2.1 cm | 2.3 cm |
| Time of beginning of flowering on previous year's cane | very late | very early | very early |
| Pedicel number of spines | few-medium | many | many |
| Intensity of anthocyanin coloration of peduncle | strong-very strong | medium-very strong | very strong |
| Time of beginning of fruit ripening on previous year's cane | late | medium | early |
| Fruiting lateral length | long | medium | medium |

-continued

| | 'Jeanne d'Orle ans' | 'Killarney' | 'Boyne' |
|---|---|---|---|
| Fruit length: | long | medium | medium |
| Fruit width: | broad | medium | medium |
| Fruit length/width ratio: | longer than broad | slightly broader than long | as long as broad |
| General shape of fruit in lateral view | broad conical-conical | circular | circular-broad conical |
| Size of single drupe of fruit | large | medium | medium |
| Fruit color | dark red (RHS 53A) | medium red (RHS 46A) | dark red (RHS 53A) |
| Adherence of fruit to plug | weak-medium | weak | very weak-weak |

I claim:

1. A new and distinct variety of raspberry plant, substantially as shown and described herein.

* * * * *

Jeanne d'Orléans